United States Patent [19]
George et al.

[11] Patent Number: 5,929,078
[45] Date of Patent: Jul. 27, 1999

[54] 1-[2-(2,3-DIHYDRO-1H-INDEN-1-YL)ETHYL]-4-(NAPHTHALEN-1-YL) PIPERAZINE, DERIVATIVES, PREPARATION THEREOF AND THERAPEUTICAL USE THEREOF

[75] Inventors: Pascal George, Saint Arnoult En Yvelines; Mireille Sevrin, Paris; Philippe Manoury, Verrieres le Buisson; Michel Peynot, L'Hay les Roses; Daniéle De Peretti, Antony; Jean François Gibert, Bretigny Sur Orge; Arlette Tixidre, Orsay; David Machnik, Paris, all of France

[73] Assignee: Synthelabo, Le Plessis Robinson, France

[21] Appl. No.: 09/011,807
[22] PCT Filed: Aug. 1, 1996
[86] PCT No.: PCT/FR96/01216
§ 371 Date: Apr. 15, 1998
§ 102(e) Date: Apr. 15, 1998
[87] PCT Pub. No.: WO97/06155
PCT Pub. Date: Feb. 20, 1997

[30] Foreign Application Priority Data

Aug. 9, 1995 [FR] France ................................. 95 09684

[51] Int. Cl.[6] ................ A61K 31/495; C07D 295/033; C07D 295/096
[52] U.S. Cl. ........................ 514/255; 544/392; 544/394
[58] Field of Search ................... 544/392, 394; 514/255

[56] References Cited

U.S. PATENT DOCUMENTS

| | | | |
|---|---|---|---|
| 2,927,924 | 3/1960 | Mills | 260/268 |
| 3,729,474 | 4/1973 | Mentrup et al. | 260/268 |
| 3,808,212 | 4/1974 | Renth et al. | 544/377 |
| 5,530,002 | 6/1996 | Manoury et al. | 544/392 |

FOREIGN PATENT DOCUMENTS

| | | |
|---|---|---|
| 0 668 273 | 8/1995 | France . |
| 2 037 852 | 2/1972 | Germany . |
| 95-18118 | 7/1995 | WIPO . |

OTHER PUBLICATIONS

Misztal et al., "Synthesis and Pharmacological Properties of N–Arylpiperazine–N'–Alkylindanes", J. Pharmacol. Pharm., vol. 36, (1984), pp. 697–703.

Primary Examiner—Emily Bernhardt
Attorney, Agent, or Firm—Foley & Lardner

[57] ABSTRACT

Compounds corresponding to the general formula (I):

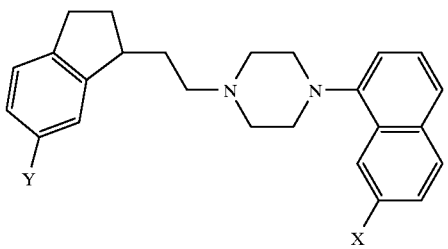

in which X represents a hydrogen atom, a hydroxyl group, a $C_1$–$C_3$ alkoxy group or a cyclopropylmethoxy group and Y represents a hydrogen atom, a hydroxyl group or a methoxy group and salts and bases thereof. The compounds may exists in the form of a pure enantiomer or as a mixture of enantiomers. Additionally, the compounds of formula (I) are useful for the treatment of diseases associated with serotoninergic receptors, particularly anxiety and/or depression.

7 Claims, No Drawings

1-[2-(2,3-DIHYDRO-1H-INDEN-1-YL)ETHYL]-4-(NAPHTHALEN-1-YL) PIPERAZINE, DERIVATIVES, PREPARATION THEREOF AND THERAPEUTICAL USE THEREOF

The subject of the present invention is 1-[2-(2,3-dihydro-1H-inden-1-yl)ethyl]-4-(naphth-1-yl)piperazine derivatives, their preparation and their application in therapeutics.

The compounds of the invention correspond to the general formula (I)

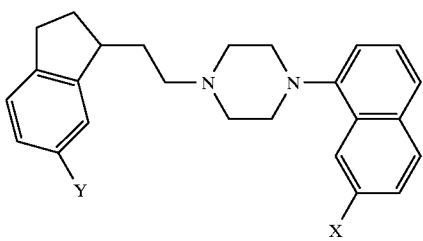

(I)

in which

X represents a hydrogen atom, a hydroxyl group, a $C_1$–$C_3$ alkoxy group or a cyclopropylmethoxy group, and Y represents a hydrogen atom, a hydroxyl group or a methoxy group.

The compounds according to the invention can exist in the form of bases or of addition salts.

Moreover, they contain, in their structure, an asymmetric carbon atom; they can therefore exist in the form of pure enantiomers or of mixtures of enantiomers.

Compounds with a chemical structure analogous to that of the compounds of general formula (I), and which can be used as medicaments for the central nervous system, are described in Patent Applications EP-0,490,772 WO 95/18118 and U.S. Pat. No. 3,729,474.

In accordance with the invention, it is possible to prepare the compounds of general formula (I) by processes illustrated by the following Schemes 1 to 3.

According to Scheme 1, a 1H-indene-3-acetic acid derivative of general formula (II), in which Y' represents a hydrogen atom or a methoxy group, is treated with a simple or complex reducing agent, such as an alkali metal or metal hydride, for example lithium aluminium hydride, borane, the borane-tetrahydrofuran or borane-dimethyl sulphide complex or alane, in an aromatic or ethereal inert solvent, for example toluene, xylene, diethyl ether, tetrahydrofuran or dioxane, at a temperature of 30 to 140° C. depending on the solvent, in order to form the alcohol of general formula (III). This alcohol is then treated with 4-methylbenzene-sulphonic acid chloride in the presence of an organic base, such as triethylamine or pyridine, and optionally in the presence of an inert solvent, at a temperature of 0 to 40° C., in order to obtain the derivative of general formula (IV). The latter is then reacted with a piperazine derivative of general formula (V), in which X is as defined above, at a temperature of 100 to 150° C., preferably at 130° C., optionally in a solvent with a high boiling point, such as toluene, xylene, N,N-dimethylformamide or 1-methylpyrrolid-2-one, in order to obtain the derivative of general formula (VI). If a final compound of general formula (I) in which Y represents a hydroxyl group is desired, a compound of general formula (VI), in which Y' represents a Scheme 1

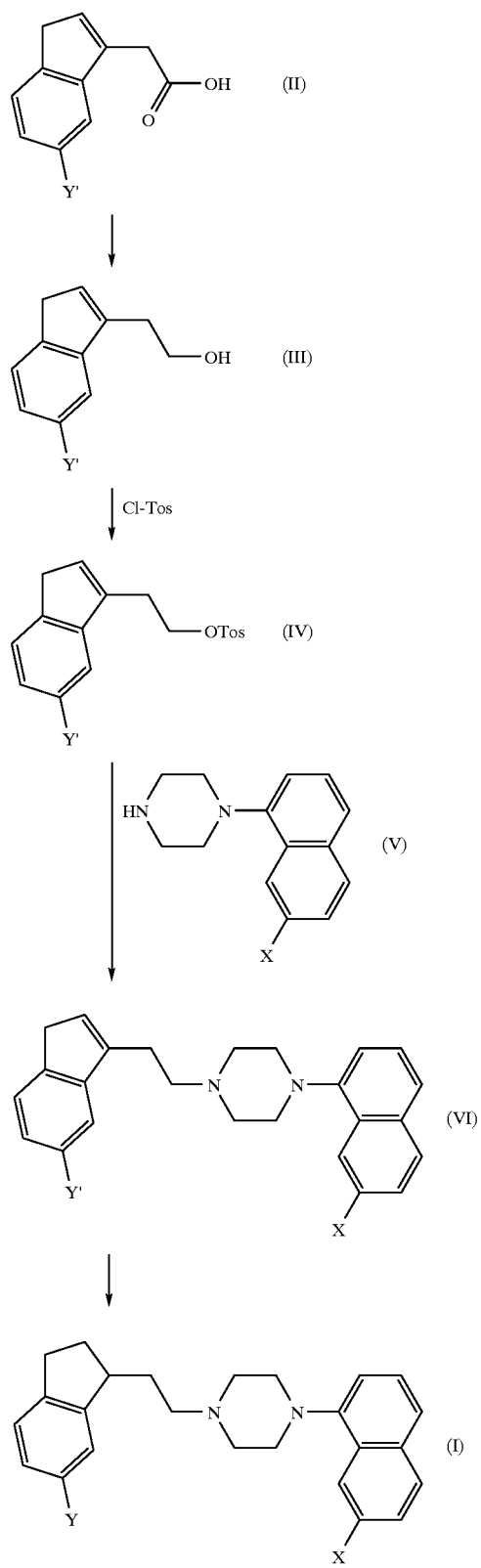

methoxy group, is demethylated by means of boron tribromide, in an inert aprotic solvent, for example dichloromethane, at a temperature of −70° C. to −5° C. Finally, the compound of general formula (VI) is reduced by catalytic hydrogenation.

According to Scheme 2, a 2,3-dihydro-1H-indene-1-ethanol derivative of general formula (VII), in which Y is as defined above, is reacted with 4-methylbenzenesulphonic acid chloride in the presence of an organic base, for example triethylamine or pyridine, optionally in an inert solvent, at a temperature of 0 to 40° C., in order to obtain a derivative of general formula (VIII). Finally, the latter is reacted with a piperazine derivative of general formula (V), in which X is as defined above, optionally in a solvent with a high boiling temperature, such as toluene or xylene, at a temperature of 100 to 150° C.

According to Scheme 3, a racemic or optically pure 2,3-dihydro-1H-indene-1-acetic acid derivative of general formula (IX), in which Y is as defined above, is treated with N,N'-carbonyldiimidazole in an inert solvent, for example a chlorinated or ethereal solvent,

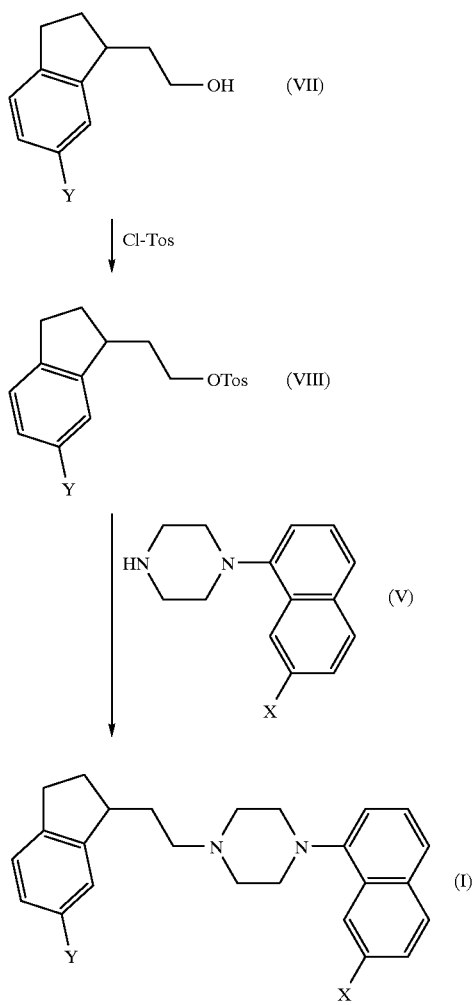

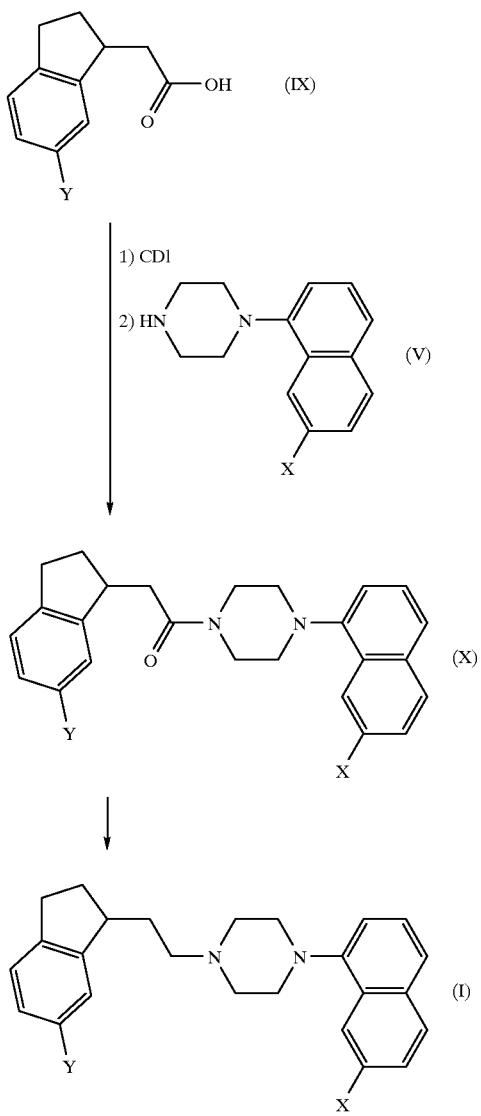

such as dichloromethane or tetrahydrofuran, at a temperature of 20 to 50° C., in order to obtain the corresponding imidazolide, the latter is then treated with a piperazine derivative of general formula (V), in which X is as defined above, in order to obtain an amide of general formula (X) and, finally, the latter is treated with a simple or complex reducing agent, such as an alkali metal or metal hydride, for example lithium aluminium hydride, in an aromatic or ethereal inert solvent, for example toluene, tetrahydrofuran or dioxane, at a temperature of 30 to 140° C., depending on the nature of the solvent.

The compounds of general formula (I) in which X and Y each represent a hydroxyl group can be obtained by conventional methods, for example by treatment of the corresponding compounds in which X and Y each represent a methoxy group with an agent such as boron tribromide, in an inert solvent such as dichloromethane, at a temperature of −20 to +40° C..

The starting acids of general formula (II) are described in C.A. 76(23) 140279s, C.A. 104(1) 5652q and J. Chem. Soc.

Perkin Trans. (1972), 1(7), 941: 2,3-dihydro-1H-inden-1-one (Y=H, commercially available) or 6-methoxy-2,3-dihydro-1H-inden-1-one (Y=OCH$_3$, described in J. Org. Chem. (1970), 35(3), 647 and J. Org. Chem. (1977), 42(12), 2155) is treated with ethyl bromoacetate in the presence of zinc powder under the conditions of the Reformatsky reaction, in order to obtain a mixture of ethyl (6-Y-2,3-dihydro-1H-inden-1-ylidene)acetate and ethyl 5-Y-1H-indene-3-acetate. Hydrolysis of this mixture in basic alcoholic medium then provides the acid of general formula (II).

The 2,3-dihydro-1H-indene-1-ethanol derivatives of general formula (VII) can be obtained according to the method described in J. Pharm. Sc. (1974), 63, 848.

The piperazine derivatives of general formula (V) are known and can be obtained by methods described in the literature, for example in Patent Applications EP-0,343,050, EP-0,354,093 and EP-0,434,561, in J. Med. Chem. (1986), 29(11), 2379, J. Med. Chem. (1988), 31(10), 1968 and in J. Med. Chem. (1991), 34(8), 2623.

The racemic acids of general formula (IX) can be obtained by catalytic hydrogenation of the mixture of esters mentioned above with respect to the starting acids of general formula (II), according to the method described in J. Am. Chem. Soc. (1952), 74, 2274, followed by hydrolysis, or by catalytic hydrogenation of these acids themselves. The optically pure starting acids of general formula (IX) can be obtained from the corresponding racemates, by resolution by means of an optically pure chiral amine, for example (+)- or (−)-α-phenylethylamine, according to J. Am. Chem. Soc. (1992), 114, 2181. They can also be obtained from the corresponding racemic esters by enantioselective hydrolysis by means of enzymes such as lipases, for example Pseudomonas or pig liver acetone powder.

The following examples illustrate in detail the preparation of the compounds according to the invention. The elemental microanalyses and the IR and NMR spectra confirm the structures of the products obtained. The numbers shown between brackets in the titles of the examples correspond to those in the first column of the table given later.

EXAMPLE 1 (COMPOUND NO. 3)

1-[2-(6-Methoxy-2,3-dihydro-1H-inden-1-yl)ethyl]-4-(7-methoxynaphth-1-yl)piperazine (E)-2-butenedioate (1:1)

1.1. 5-Methoxy-1H-indene-3-ethanol.

A suspension of 0.76 g (0.02 mol) of lithium aluminium hydride in 50 ml of diethyl ether is prepared, a solution of 2.04 g (0.01 mol) of 5-methoxy-1H-indene-3-acetic acid is added and the mixture is stirred and heated at reflux for 32 h. The mixture is allowed to cool, is hydrolysed with 1.6 ml of a 10% aqueous potassium sodium tartrate solution, is reheated to boiling point for 1 h and is filtered, the residue being rinsed with tetrahydrofuran, and the filtrate is evaporated under reduced pressure. 1.8 g of an oily residue are obtained, which residue is purified by distillation. 1.55 g of a yellow liquid are obtained, which liquid is used as is in the following stage.

1.2. 2-(5-Methoxy-1H-inden-3-yl)ethyl 4-methylbenzenesulphonate 1.27 g (0.0067 mol) of 5-methoxy-1H-indene-3-ethanol are dissolved in 11 ml of dry pyridine, the mixture is stirred, is cooled with an ice bath, 1.4 g (0.0073 mol) of 4-methylbenzenesulphonic acid chloride are added portionwise and stirring is maintained overnight while cold and then at room temperature for 4 h. The solution is poured onto a mixture of 16 ml of 10N hydrochloric acid and 48 g of ice, the mixture obtained is treated with diethyl ether, the organic phase is separated, is washed with water, in dried over magnesium sulphate and is filtered and the filtrate is evaporated under reduced pressure. 1.94 g of a colourless oily product are obtained, which product is used as is in the following stage.

1.3. 1-[2-(5-Methoxy-1H-inden-3-yl)ethyl]-4-(7-methoxynaphth-1-yl)piperazine 2.07 g (0.006 mol) of 2-(5-methoxy-1H-inden-3-yl)ethyl 4-methylbenzenesulphonate and 2.90 g (0.012 mol) of 1-(7-methoxynaphth-1-yl)piperazine are mixed and the mixture is stirred, is placed under an argon atmosphere and is heated in an oil bath at 130° C. for 2 h. The mixture is taken up in dichloromethane, the solution is washed with water, with dilute sodium hydroxide and then again with water, is dried over magnesium sulphate and is filtered and the filtrate is evaporated under reduced pressure. 4.08 g of an oil are obtained, which oil is purified by chromatography on a column of silica gel, elution being carried out with a 92/8 dichloromethane/acetone mixture.

2.09 g of compound are obtained.

1.4. 1-[2-(6- Methoxy-2,3-dihydro-1H-inden-1-yl)ethyl]-4-(7-methoxynaphth-1-yl)piperazine (E)-2-butenedioate (1:1)

0.9 g (0.0021 mol) of 1-[2-(5-methoxy-1H-inden-3-yl)ethyl]-4-(7-methoxynaphth-1-yl)piperazine is dissolved in 40 ml of ethanol, 0.17 ml (1 equivalent) of chloroform and 0.4 g of 10% palladium-on-charcoal are added and hydrogenation in carried out in a Parr apparatus under a pressure of approximately 0.3 MPa. When the theoretical amount of hydrogen has been absorbed, the catalyst is separated by filtration and the filtrate is evaporated under reduced pressure. The residue is taken up in dichloromethane and water, potassium carbonate is added, the organic phase is separated, is washed with water and is dried over sodium sulphate and the solvent is evaporated under reduced pressure. 0.76 g of an oily product is obtained, which product is dissolved in ethanol, 0.21 g (1 equivalent) of fumaric acid is added and the salt which precipitates is separated and is recrystallized from ethanol.

Melting point: 133–135° C.

EXAMPLE 2 (COMPOUND NO. 2)

1-[2-(2,3-Dihydro-1H-inden-1-yl)ethyl]-4-(7-methoxynaphth-1-yl)piperazine (E)-2-butenedioate (1:1)

2.1. 2-(2,3-Dihydro-1H-inden-1-yl)ethyl 4-methylbenzenesulphonate.

2.2 g (0.0136 mol) of 2,3-dihydro-1H-indene-1-ethanol are dissolved in 25 ml of dry pyridine, the solution is stirred and is cooled with an ice bath, 2.6 g (0.0136 mol) of 4-methylbenzonesulphonic acid chloride are added portionwise and stirring is maintained for 1 h at 0° C. and then for 3 h at room temperature. The solution obtained is poured onto a mixture of 50 ml of 10N hydrochloric acid and 100 g of ice, diethyl ether is added, the organic phase is separated, is washed with water, is dried over magnesium sulphate and is filtered and the solvent is evaporated under reduced pressure.

2.5 g of a colourless oily product are obtained, which product is used as is in the following stage.

2.2. 1-[2-(2,3-Dihydro-1H-inden-1-yl)ethyl]-4-(7-methoxynaphth-1-yl)piperazine (E)-2-butenedioate (1:1)

A mixture of 1.1 g (0.0035 mol) of 2-(2,3-dihydro-1H-inden-1-yl)ethyl 4-methylbenzenesulphonate and 1.7 g (0.007 mol) of 1-(7-methoxynaphth-1-yl)piperazine is prepared and is heated under an argon atmosphere in an oil bath at 130° C. for 3 h. The mixture is allowed to cool, is treated with aqueous sodium hydroxide and is extracted with dichloromethane. The organic phase is washed with water, is dried over magnesium sulphate and is filtered and the solvent is evaporated under reduced pressure. 2.2 g of an oily product are obtained, which product is purified by chromatography on a column of silica gel, elution being carried out with a 97/3 mixture of dichloromethane and acetone. 1.3 g of purified base are obtained, which base is dissolved in a mixture of propan-2-ol and diethyl ether, a solution of 0.4 g of fumaric acid dissolved in hot propan-2-ol is added and the mixture in heated and is allowed to cool slowly. After recrystallizing from ethanol, 1.2 g of fumarate are finally obtained.

Melting point: 185–186° C.

EXAMPLE 3 (COMPOUND NO. 13)

(−)-1-[2-(6-Methoxy-2,3-dihydro-1H-inden-1-yl)ethyl]-4-(7-methoxynaphth-1-yl)piperazine (E)-2-butenedioate (1:1)

3.1. (±)-2,3-Dihydro-6-methoxy-1H-indene-1-acetic acid.

4.97 g (0.028 mol) of 5-methoxy-1H-indene-3-acetic acid are dissolved in 100 ml of glacial acetic acid, 2.6 g of 10% palladium-on-charcoal are added and hydrogenation is carried out in a Parr apparatus under approximately 0.3 MPa. When the theoretical amount of hydrogen has been absorbed, the catalyst is separated by filtration, the filtrate is evaporated under reduced pressure, the residue is taken up a number of times in cyclohexane, which is evaporated in order to drive off any trace of acetic acid, and, after drying under reduced pressure, 4.04 g of solid are obtained.

Melting point: 90–92° C.

3.2. (−)-2,3-Dihydro-6-methoxy-1H-indene-1-acetic acid a) 4.04 g (0.02 mol) of (±)-2,3-dihydro-6-methoxy-1H-indene-1-acetic acid are dissolved in 70 ml of acetone, 2.06 g (0.017 mol) of (R)-α-phenylethylamine are added and the mixture is stirred at room temperature for 4 h. The white solid is collected by filtration and is recrystallized a number of times from acetone, until a constant melting point is obtained.

Melting point: 166.5–167.5° C.

$[\alpha]_D^{20}$=−9.2° (c=0.31, CH$_3$OH).

b) The salt thus obtained is treated with a 0.25N sodium hydroxide solution, the pH being brought to 10, the amine released is extracted with benzene and the aqueous phase is acidified with concentrated hydrochloric acid to pH=1 and is extracted three times with diethyl ether. The ethereal organic phase is washed with water and is dried over sodium sulphate, the solvent is evaporated under reduced pressure and the solid is recrystallized from a mixture of hexane and petroleum ether.

Melting point: 88–89° C.

$[\alpha]_D^{20}$=−40.0° (c=0.80, CH$_3$OH), ee=99.3% (HPLC)

3.3. (−)-1-[(2,3-Dihydro-6-methoxy-1H-inden -1-yl)acetyl]-4-(7-methoxynaphth-1-yl)piperazine 0.26 g (1.3 mmol) of (−)-2,3-dihydro-6-methoxy-1H-indene-1-acetic acid is introduced, under a nitrogen atmosphere, into 7 ml of dry tetrahydrofuran, 0.265 g (1.6 mmol) of N,N'-carbonyldiimidazole is added portionwise and the mixture is stirred at room temperature for 1 h 30. 0.336 g (1.4 mmol) of 4-(7-methoxynaphth-1-yl)piperazine, in solution in 2 ml of dry tetrahydrofuran, is added and the mixture is stirred at room temperature for 16 h. The solvent is evaporated under reduced pressure, the residue is taken up in water and dichloromethane, the organic phase is separated, is washed with a saturated aqueous sodium chloride solution and then with water and is dried over sodium sulphate, the solvent is evaporated under reduced pressure and the residue is purified by chromatography on a column of silica gel, elution being carried out with a 97/3 mixture of dichloromethane and acetone. 0.49 g of compound is obtained.

Melting point: 57–60° C.

$[\alpha]_D^{20}$=−25.8° (c=0.48, CH$_3$OH).

3.4. (−)-1-[2-(6-Methoxy-2,3-dihydro-1H-inden-1-yl)ethyl]-4-(7-methoxynaphth-1-yl)piperazine (E)-2-butenedioate (1:1)

0.06 g (1.6 mmol) of lithium aluminium hydride is introduced, under a nitrogen atmosphere, into 3 ml of dry tetrahydrofuran, 0.4 g (0.93 mmol) of (−)-1-[(2,3-dihydro-6-methoxy-1-inden-1-yl)acetyl]-4-(7-methoxynaphth-1-yl)piperazine, in solution in 2 ml of dry tetrahydrofuran, is added dropwise and the mixture is heated at reflux for 2 h 30. 5 ml of ethyl acetate are added, the mixture is stirred for 15 min and is filtered, the filtrate is evaporated under reduced pressure, the residue is taken up in ethyl acetate and a saturated aqueous sodium chloride solution, the organic phase is separated, is washed with water and is dried over sodium sulphate and the solvent is evaporated under reduced pressure. 0.38 g of an oily product is obtained, the product is dissolved in propan-2-ol, 0.1 g of fumaric acid dissolved in hot propan-2-ol is added and the mixture is heated and is allowed to cool slowly. After recrystallizing from ethanol, 0.3 g of fumarate is obtained.

Melting point: 171–172° C.

$[\alpha]_D^{20}$=−22.0° (c=0.40, CH$_3$OH), ee>99.8% (HPLC).

EXAMPLE 4 (COMPOUND NO. 14)

(+)-1-[2-(6-Methoxy-2,3-dihydro-1H-inden-1-yl)ethyl]-4-(7-methoxynaphth-1-yl)piperazine (E)-2-butenedioate (1:1)

4.1. (+)-2,3-Dihydro-6-methoxy-1H-indene-1-acetic acid.

a) The mother liquors resulting from the recrystallizations of the salt obtained in Example 3.2.a) are combined, the solvent is evaporated under reduced pressure, the residue is dissolved in water, the pH is adjusted to 10 with a 0.25N aqueous sodium hydroxide solution, the amine released is extracted with benzene and the aqueous phase is acidified and is extracted three times with diethyl ether. The ethereal organic phase is washed with water and is dried over sodium sulphate and the solvent is evaporated under reduced pressure. 2.8 g of solid are obtained, which solid is recrystallized from hexane.

b) 1.95 g (0.95 mmol) of this solid are dissolved in 20 ml of acetone, 1.1 g (0.9 mmol) of (S)-α-phenylethylamine, in solution in 5 ml of acetone, are added thereto dropwise and the mixture is stirred at room temperature for 1 h 30. The solid is collected by filtration, is dried and is recrystallized a number of times from acetone, until a constant melting point is obtained. 0.8 g of salt is obtained.

Melting point: 165.5–167.5° C.

$[\alpha]_D^{20}$=+11.5° (c=0.46, CH$_3$OH).

c) 0.76 g of this salt is treated with a 0.25N sodium hydroxide solution to pH=10, the amine released is extracted with benzene, the aqueous phase is acidified with concentrated hydrochloric acid to pH=1 and is extracted three times with diethyl ether, the ethereal organic phase is washed with a saturated aqueous sodium chloride solution and is dried over sodium sulphate, the solvent is evaporated under reduced pressure and the residue is recrystallized from hexane. 0.42 g of compound is obtained.

Melting point: 86.5–87.5° C.

$[\alpha]_D^{20}$=+20.9° (c=0.66, CH$_3$OH), ee=95.2% (HPLC).

4.2. (+)-1-[(2,3-Dihydro-6-methoxy-1H-inden-1-yl)acetyl]-4-(7-methoxynaphth-1-yl)piperazine By using the method described in Example 3.3, and starting from 0.36 g (1.7 mmol) of (+)-2,3-dihydro-6-methoxy-1H-indene-1-acetic acid and 0.464 g (1.9 mmol) of 4-(7-methoxynaphth-1-yl)piperazine, 0.62 g of compound is obtained.

Melting point: 55–58° C.

$[\alpha]_D^{20}$=+26.1° (c=0.54, CH$_3$OH).

4.3. (+)-1-[2-(6-Methoxy-2,3-dihydro-1H-inden-1-yl)ethyl]-4-(7-methoxynaphth-1-yl)piperazine (E)-2-butenedioate (1:1)

By using the method described in Example 3.4, and starting from 0.535 g (1.2 mmol) of (+)-1-[(2,3-dihydro-6-methoxy-1H-inden-1-yl)acetyl]-4-(7-methoxynaphth-1-yl)piperazine and 0.1 g (2.6 mmol) of lithium aluminium hydride, 0.47 g of amine is obtained, from which amine 0.495 g of fumarate is prepared.

Melting point: 169–170° C.

$[\alpha]_D^{20}$=+23.0° (c=0.46, CH$_3$OH), ee=95.4% (HPLC).

EXAMPLE 5 (COMPOUND NO. 11)

(R)-(+)-1-[2-(2,3-Dihydro-1H-inden-1-yl)ethyl]-4-(7-methoxynaphth-1-yl)piperazine (E)-2-butenedioate (1:1)

5.1. Ethyl (±)-2,3-dihydro-1H-indene-1-acetate.

12 g (0.06 mol) of a mixture of ethyl (2,3-dihydro-1H-inden-1-ylidene)acetate and ethyl 1H-indene-3-acetate, described in J. Am. Chem. Soc. (1952), 74, 2274, are dissolved in 250 ml of ethanol, 1.5 g of 10% palladium-on-charcoal are added and hydrogenation is carried out in a Parr apparatus under a pressure of approximately 0.3 MPa. When the theoretical amount of hydrogen has been absorbed, the catalyst is separated by filtration, the solvent is evaporated under reduced pressure and the residue is distilled. 11.8 g of liquid are obtained, which liquid is used as is.

Boiling point: 160° C. (270 Pa/2 mm Hg).

5.2. Ethyl (R)-(+)-2,3-dihydro-1H-indene-1-acetate 2.88 g of Pseudomonas lipase PS (Amano®) are added to 24 g (0.117 mol) of ethyl (±)-2,3-dihydro-1H-indene-1-acetate in solution in 160 ml of diisopropyl ether and 160 ml of 0.01M phosphate buffer (potassium dihydrogenphosphate and disodium hydrogenphosphate), at pH=7.8, and the mixture in stirred for 24 h, the pH being kept constant by addition of a 5N aqueous sodium hydroxide solution. The pH is adjusted to 9 and the mixture in extracted three times with diisopropyl ether, the organic phase is dried over magnesium sulphate and the solvent is evaporated under reduced pressure. 10.8 g of compound are obtained.

$[\alpha]_D^{20}$=+11.6° (c=1.05, CHCl$_3$), ee=99% (HPLC).

5.3. (R) -(+)-2,3-Dihydro-1H-indene-1-acetic acid

A mixture of 23.5 g (0.11 mol) of ethyl (R)-(+)-2,3-dihydro-1H -indene-1-acetate and 32.6 g (0.58 mol) of potassium hydroxide is heated in 600 ml of a 50/50 mixture of water and ethanol at reflux for 1 h. The ethanol is evaporated under reduced pressure, the aqueous phase is extracted with diethyl ether, is acidified to pH=1 with concentrated hydrochloric acid and is extracted three times with diethyl ether, the organic phase is washed with water and is dried over sodium sulphate, the solvent is evaporated under reduced pressure and 18 g of solid are obtained, which solid is recrystallized from n-hexane.

Melting point: 78.5–80.5° C.

$[\alpha]_D^{20}$=+8.1° (c=1.21, CH$_3$COCH$_3$), ee=99% (HPLC).

5.4. (R)-(+)-1-[(2,3-Dihydro-1H-inden-1-yl)acetyl]-4-(7-methoxynaphth-1-yl)piperazine By using the method described in Example 3.3, and starting from 2.3 g (13 mmol) of (R)-(+)-2,3-dihydro-1H-indene-1-acetic acid and 3.4 g (14 mmol) of 4-(7-methoxynaphth-1-yl)piperazine, 4.3 g of compound are obtained.

Melting point: 121–123° C.

$[\alpha]_D^{20}$=+8.5° (c=0.46, CH$_3$COCH$_3$).

5.5. (R)-(+)-1-[2-(2,3-Dihydro-1H-inden-1-yl)ethyl]-4-(7-methoxynaphth-1-yl)piperazine (E)-2-butenedioate (1:1)

By using the method described in Example 3.4, and starting from 4.2 g (10 mmol) of (R)-(+)-1-[(2,3-dihydro-1H-inden-1-yl) acetyl] -4-(7-methoxynaphth-1-yl) piperazine, by the action of 0.4 g (10 mmol) of lithium aluminium hydride and then of 0.96 g (8.3 mmol) of fumaric acid, 3.7 g of compound are obtained.

Melting point: 177–179° C.

$[\alpha]_D^{20}$=+3.9° (c=1, CH$_3$OH), ee=97.5% (HPLC).

The chemical structures and the physical properties of some compounds according to the invention are illustrated in the following table.

TABLE

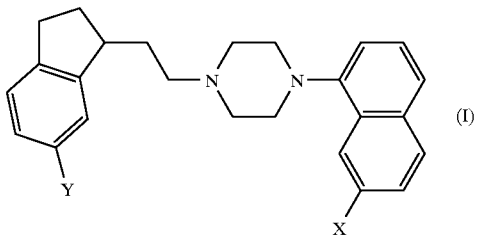

(I)

| No. | X | Y | Isom. | Salt | M.p. (° C.) |
|---|---|---|---|---|---|
| 1 | H | H | RS | fum. (1:1) | 198–200 |
| 2 | OCH$_3$ | H | RS | fum. (1:1) | 185–186 |
| 3 | OCH$_3$ | OCH$_3$ | RS | fum. (1:1) | 133–135 |
| 4 | OCH$_2$CH$_3$ | H | RS | fum. (1:1) | 182–183 |
| 5 | OCH$_2$CH$_3$ | OCH$_3$ | RS | fum. (1:1) | 104–105 |
| 6 | OCH$_2$CH$_2$CH$_3$ | OCH$_3$ | RS | fum. (1:1) | 97–98 |
| 7 | OCH(CH$_3$)$_2$ | OCH$_3$ | RS | fum. (1:1) | 155.5–157 |
| 8 | OCH$_2$cC$_3$H$_5$ | H | RS | fum. (1:1) | 169.5–171 |
| 9 | OH | OCH$_3$ | RS | HCl (1:1) | 271–273.5 (d) |
| 10 | OH | OH | RS | HCl (1:1) | 168–170 |
| 11 | OCH$_3$ | H | R-(+) | fum. (1:1) | 177–179 |
|  |  |  |  | mes. (1:1) | 129.5–131 |
| 12 | OCH$_3$ | H | S-(−) | fum. (1:1) | 174.5–177.5 |
| 13 | OCH$_3$ | OCH$_3$ | (−) | fum. (1:1) | 171–172 |
| 14 | OCH$_3$ | OCH$_3$ | (+) | fum. (1:1) | 169–170 |

Key

In the "X" column, "OCH$_2$cC$_3$H$_5$" denotes a cyclopropylmethoxy group. In the "Salt" column, "−" denotes a compound in the base form, "fum." denotes a fumarate or (E)-2-butenedioate, "HCl" denotes a hydrochloride and "mes." denotes a mesylate or methanesulphonate; the ratio shown between brackets is the base:acid molar ratio. In the "M.p.(° C.)" column, "(d)" denotes a melting point with decomposition.

The compounds of the invention have formed the subject of tests which have demonstrated their advantage as therapeutic substances.

Thus, they have been tested in vitro with respect to their affinity for type 5-HT$_{1A}$ serotoninergic receptors present in the rat hippocampus, according to a protocol described by Sanger and Schoemaker, *Psychopharmacology* (1992), 108, 85–92. The compounds displace the binding of a labelled specific ligand, [$^3$H]-8-hydroxy-2-(di-n-propylamino) tetralin (hereinafter denoted by "[$^3$H]-8-OH-DPAT" and described by Gozlan et al., Nature (1983), 305, 140–142), with respect to 5-HT$_{1A}$ receptors. The animals used are male Sprague-Dawley rats weighing 160 to 200 g. After decapitation, the brain is removed therefrom and the hippocampus is excised. The tissue is milled in an Ultra-Turrax Polytron apparatus for 30 s at half the maximum speed in 10 volumes of 50 mM Tris buffer at a pH adjusted to 7.4 with hydrochloric acid (i.e. 100 mg of fresh tissue per ml). The homogenized tissues are washed three times at 4° C., the tissues being centrifuged each time for 10 min at 48,000× and the pellet being resuspended in fresh cooled buffer. Finally, the last pellet is suspended in the buffer to produce a concentration of 100 mg of starting tissue per ml of 50 mM buffer. Incubation is then allowed to take place at 37° C. for 10 min. Binding with [$^3$H]-8-OH-DPAT (1 nM) is determined by incubating 100 µl of membrane suspension in a final volume of 1 ml of buffer containing 10 µM of pargyline and 3 µM of paroxetine. After incubating for 15 min at 37° C., the membranes are recovered by filtering through Whatman GF/B® filters, which are washed three times with 5 ml aliquot amounts of ice-cold buffer. The filters are extracted in the liquid scintillant and the radioactivity thereof is measured by liquid scintigraphy. The specific binding of the [$^3$H]-8-OH-DPAT is defined as the radioactive amount retained on the filters which can be inhibited by co-incubation in 10 µM 5-hydroxytryptamine. At a [$^3$H]-8-OH-DPAT concentration of 1 nm, the specific binding represents 90% of the total radioactivity recovered on the filter. For each concentration of compound studied, the percentage of inhibition of the binding with [$^3$H]-8-OH-DPAT is determined and then the IC$_{50}$ concentration, the concentration which inhibits 50% of the binding, is determined. The IC$_{50}$ values lie between 1 and 300 nM.

The compounds of the invention have also formed the subject of an in vitro study with respect to their affinity for the 5HT$_{1D}$ serotoninergic receptors present in the bovine caudate nucleus, demonstrated by the displacement of a labelled specific ligand, [$^3$H]-5-hydroxytryptamine, essentially as described by Heuring and Peroutka in J. Neurosci., (1987), 7, 804–903. The bovine caudate nucleus (Collectorgane, Paris) is stored at −80° C. until use. The tissue is milled in an Ultra-Turrax Polytron apparatus for 30 s at half the maximum speed in 10 volumes of 50 mM Tris buffer, the pH of which is adjusted to 7.4 with hydrochloric acid (i.e. 100 mg of fresh tissue per ml). The homogenized tissues are washed twice at 4° C. and centrifuged for 10 min at 40,000×, the pellet being resuspended each time in ice-cold buffer. Finally, the last pellet is suspended in buffer to produce a concentration of 100 mg of starting tissue per ml of 50 mM buffer and allowed to incubate at 37° C. for 15 min. The membrane suspension is then centrifuged for 10 min at 40,000× and the pellet is resuspended in 8 volumes of incubation medium containing Tris (50 mM), ascorbic acid (0.1%), calcium chloride (4 mM), pargyline (10 µM), mesulergine (100 nM) and 8-hydroxydipropylaminotetralin (100 nM), the pH of which is adjusted to 7.4 with hydrochloric acid. The binding with [$^3$H]-5-hydroxytryptamine (2 nM) is determined by incubating 100 µl of membrane suspension in a final volume of 1 ml of incubation medium. After incubating for 30 min at 37° C., followed by incubating for 5 min between 0 and 4° C., the membranes are recovered by filtration through Whatman GF/B® filters, which are washed twice with 1 ml aliquot amounts of ice-cold 50 mM Tris buffer, the pH of which is adjusted to 7.4 with hydrochloric acid. The filters are extracted in the liquid scintillant and the radioactivity is measured by liquid scintigraphy. The specific binding of the [$^3$H]-5-hydroxytryptamine is defined as the amount of radioactivity retained on the filters which can be inhibited by co-incubation with 0.1 µM 5-hydroxytryptamine. At a [$^3$H]-5-hydroxytryptamine concentration of 2 nM, the specific binding represents 70% of the total radioactivity recovered on the filter. For each concentration of compound studied, the percentage of inhibition of the binding with [$^3$H]-5-hydroxytryptamine is determined and then the IC$_{50}$ concentration, the concentration which inhibits 50% of the binding, is determined. The most active compounds of the invention have, in this test, an IC$_{50}$ value of less than 40 nM.

The compounds of the invention have also formed the subject of an in vitro test of displacement of the binding of spiperone with respect to the serotoninergic receptors (5-HT$_2$) of the cerebral cortex of the rat. For this test, rat brains are removed, the cortex is dissected therefrom and is homogenized at 0° C. in 10 volumes of a mixture containing, per liter, 50 millimol of Tris/HCl buffer at pH=7.4, 120 millimol of sodium chloride and 5 millimol of potassium chloride. The homogeneous mixture is centrifuged at 40,000× for 10 min and then, with two repetitions, the pellet is recovered, is washed by suspending it in the same buffer mixture, is rehomogenized and in centrifuged. For completion, the final pellet is diluted in the same buffer mixture in the proportion of 100 mg of wet tissue per 1 ml of buffer. The tissue is then subjected to a prior incubation for is 10 min at 37° C. in the presence of 10 micromol/l of pargyline and then to an incubation for 20 min at 37° C. in the presence of $^3$H-spiperone (specific activity: 15 to 30 Ci per millimol) at a concentration of 0.3 nanomol/l and of the study compound. The membranes are then recovered by filtration through Whatman GF/B® filters, which are washed twice with 5 ml of cold buffer. The radioactivity retained on the filter is measured by liquid scintigraphy. In order to evaluate the activity of the compounds, the curve of the percentage of inhibition of the specific binding of $^3$H-spiperone as a function of the concentration of the displacing drug is drawn up. The IC$_{50}$ concentration, the concentration which inhibits 50% of the specific binding, is determined graphically. The specific binding is defined as being the binding displaced by 100 micromol/l of 5-HT. The IC$_{50}$ concentrations of the compounds of the invention lie between 50 and 1500 nM.

Finally, the compounds of the invention have formed the subject of an in vitro study with respect to their affinity for the 5HT$_{1C}$ serotoninergic receptors present in the pig choroid plexus, demonstrated by the displacement of the binding of a labelled specific ligand, [$^3$H]mesulergine, essentially as described by Pazos et al., in Eur. J. Pharmacol., (1984), 106, 539–546 and by Yagalof and Rartig in Mol. Pharmacol., (1986), 26, 120–125. The choroid plexus (Collectorgane, Paris) is stored at −80° C. until use. The tissue is homogenized in a Potter homogenizer with 10 to 15 bursts (800 rpm) in 10 volumes of sucrose (0.32 M) at a temperature of 0 to 4° C. The membrane suspension is centrifuged for 10 min at 1,000× (4° C.) and the supernatant is centrifuged for 20 min at 30,000× (4° C.). The pellet is suspended in 10 volumes of 50 mM Tris buffer with a pH adjusted to 7.4 with hydrochloric acid and is then incubated at 37° C. for 15 min. Finally, the suspension is centrifuged for 20 min at 30,000× (4° C.) and the pellet is taken up again in 28 volumes of incubation buffer containing Tris (50 mM), ascorbic acid (0.1%), calcium chloride (4 mM) and pargyline (10 µM), the pH of which is adjusted to 7.4 with hydrochloric acid. The binding with [³H]mesulergine (1 nM) is determined by incubating 100 μl of membrane suspension in a final volume of 500 μl of incubation medium. After incubating for 30 min at 37° C., followed by incubating for 5 min between 0 and 4° C., the membranes are recovered by filtration through Whatman GF/B® filters, which filters were pretreated for 30 min with 0.05% polyethylenimine, and the membranes are washed with two times 1 ml of ice-cold 50 mM Tris buffer, the pH of which is adjusted to 7.4 with hydrochloric acid. The filters are extracted in the liquid scintillant and the radioactivity is measured by liquid scintigraphy. The specific binding of the [³H]mesulergine is defined as the amount of radioactivity retained on the filters which can be inhibited by co-incubation with 10 μM 5-hydroxytryptamine. At a [³H] mesulergine concentration of 1 nM, the specific binding represents 90% of the total radioactivity recovered on the filter. For each concentration of compound studied, the percentage of inhibition of the binding with [³H]mesulergine is determined and then the $IC_{50}$ concentration, the concentration which inhibits 50% of the binding, is determined. The compounds of the invention have, in this test, $IC_{50}$ values of 5 to 500 nM.

The results of the test show that the compounds of the invention have a strong affinity for serotoninergic receptors of $5HT_{1A}$, $5HT_{1B}$ and $5HT_{1C}$ types and a moderate affinity for $5HT_2$ receptors.

These results suggest that the compounds can be used in the treatment of all conditions related to disfunctionings of serotoninergic receptors of $5HT_{1A}$, $5HT_{1D}$, $5HT_{1C}$ and/or $5HT_2$ types, in particular in the treatment of anxiety states, depression, including psychotic depression, sleep disorders, phobias, panic states, obsessive compulsive disorders, disorders due to abuse of or withdrawal from alcohol or drugs, productive or deficient schizophrenia, acute or chronic extrapyramidal syndromes induced by neuroleptics, or disorders of sexual behaviour, in the regulation of food intake and also in the treatment of vascular or cardiovascular disorders, such as migraine and hypertension.

To this end, they can be presented in all pharmaceutical forms suitable for enteral or parenteral administration, in association with appropriate excipients, for example in the form of tablets, dragées, capsules, including hard gelatin capsules, suppositories or solutions or suspensions to be taken orally or to be injected, at doses which make possible a daily administration of 1 to 1000 mg of active substance.

What is claimed is:

1. A compound of formula (I)

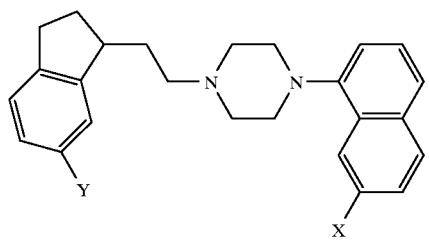

(I)

in which
X represents a hydrogen atom, a hydroxyl group, a $C_1$–$C_3$ alkoxy group or a cyclopropylmethoxy group, and
Y represents a hydrogen atom, a hydroxyl group or a methoxy group,
in the form of a base or of an addition salt and in the form of a pure enantiomer or of a mixture of enantiomers.

2. A pharmaceutical composition comprising a compound according to claim 1 and a pharmaceutically acceptable excipient.

3. A process for the preparation of a compound according to claim 1, comprising:

reacting a 1H-inden-3-acetic acid derivative of general formula (II)

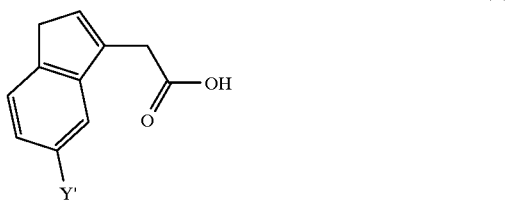

(II)

in which Y' represents a hydrogen atom or a methoxy group, with a reducing agent, to form an alcohol of general formula (III):

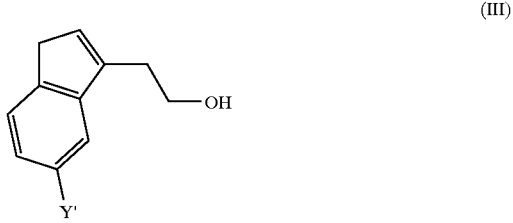

(III)

subsequently reacting the compound of formula (III) with p-toluenesulphonyl chloride, to form a derivative of general formula (IV)

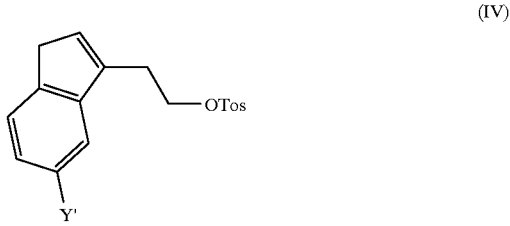

(IV)

subsequently reacting the compound of formula (IV) with a piperazine derivative of general formula (V)

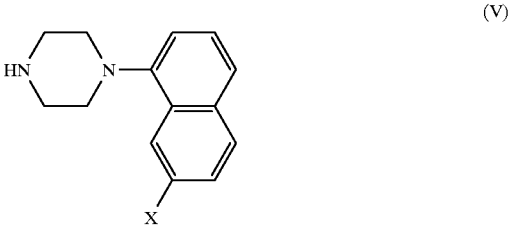

(V)

wherein X is as defined in claim 1, to form a derivative of general formula (VI)

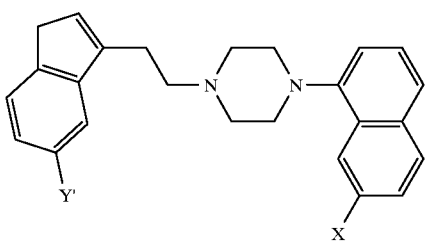
(VI)

subsequently optionally demethylating the compound of formula VI in which Y' is defied as a methoxy group to form a compound wherein Y' is hydroxy and then reducing the compound by catalytic hydrogenation to yield a compound of formula I.

4. A process for the preparation of a compound according to claim 1, comprising:
reacting a 2,3-dihydro-1H-indene-1-ethanol derivative of general formula (VII)

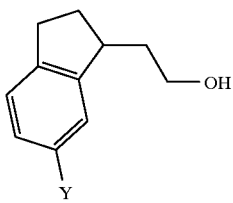
(VII)

wherein Y represents a hydrogen atom or a methoxy group,
with p-toluensulphonyl chloride, to form a derivative of general formula (VIII)

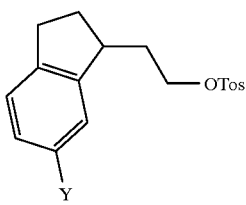
(VIII)

and, subsequently reacting a compound of formula (VIII) with a piperazine derivative of general formula (V)

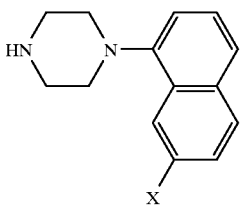
(V)

wherein X is as defined in claim 1, to yield a compound of formula I wherein Y is hydrogen or methoxy, and optionally demethylatine to form compounds of formula I wherein Y is hydroxy.

5. A process for the preparation of a compound according to claim 1, comprising:

reacting a racemic or optically pure 2,3-dihydro-1H-indene-1-acetic acid derivative of general formula (IX)

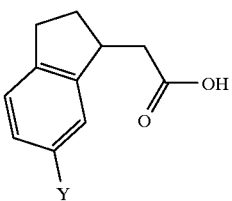
(IX)

wherein Y represents a hydrogen atom, a hydroxyl group or a methoxy group, with N,N-carbonyldiimidazole, to form the corresponding imidazolide, subsequently reacting the thus formed imidazolide with a piperazine derivative of general formula (V)

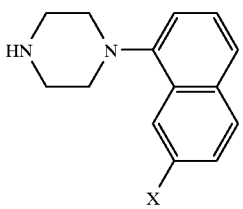
(V)

wherein X is as defined in claim 1 to form an amide of general formula (X)

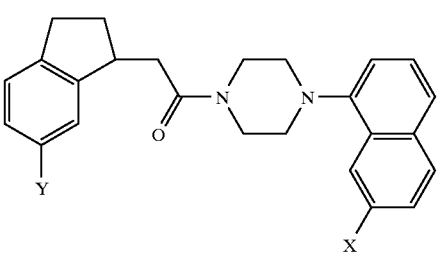
(X)

and subsequently reacting the compound of formula (X) with a reducing agent to form a compound of formula I.

6. A compound according to claim 1, selected from the group consisting of:

1-[2-(6-methoxy-2,3-dihydro-1H-inden-1-yl)-ethyl]-4-(7-methoxynaphth-1-yl) piperazine;

1-[2-(2,3-dihydro-1H-inden-1-yl)-ethyl]-4-(7-methoxynaphth-1-yl) piperazine;

(−)-1-[2-(6-methoxy-2,3-dihydro-1H-inden-1-yl)-ethyl]-4-(7-methoxynaphth-1-yl) piperazine;

(+)-1-[2-(6-methoxy-2,3-dihydro-1H-inden-1-yl)-ethyl]-4-(7-methoxynaphth-1-yl) piperazine;

(R)-(+)-1-[2-(2,3-dihydro-1H-inden-1-yl)-ethyl]-4-(7-methoxynaphth-1-yl) piperazine; and addition salts thereof.

7. A method of treating a disease selected from the group consisting of anxiety, depression, hypertension, and migraine comprising administering to a patient in need thereof an effective amount of a compound of formula (I):

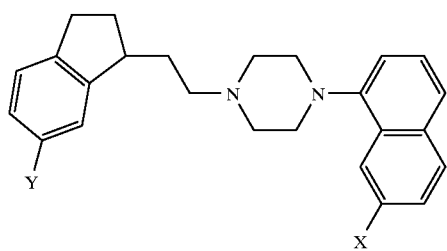
in which
X represents a hydrogen atom, a hydroxyl group, a $C_1$–$C_3$ alkoxy group or a cyclopropylmethoxy group, and Y represents a hydrogen atom, a hydroxyl group or a methoxy group, in the form of a base or an addition salt and in the form of a pure enantiomer or of a mixture of enantiomers.
\* \* \* \* \*